(12) United States Patent
Bub et al.

(10) Patent No.: US 7,294,741 B2
(45) Date of Patent: Nov. 13, 2007

(54) PROCESS FOR THE PRODUCTION OF ACRYLIC ACID

(75) Inventors: Gunther Bub, Marl (DE); Jurgen Mosler, Castrop-Rauxel (DE); Dietrich Maschmeyer, Recklinghausen (DE); Andreas Sabbagh, Moers (DE); Roland Fornika, Dulmen (DE); Matthias Peuckert, Hunxe (DE)

(73) Assignee: Stockhausen GmbH, Krefeld (DE)

( * ) Notice: Subject to any disclaimer, the term of this patent is extended or adjusted under 35 U.S.C. 154(b) by 242 days.

(21) Appl. No.: 10/498,852

(22) PCT Filed: Dec. 13, 2002

(86) PCT No.: PCT/EP02/14227

§ 371 (c)(1),
(2), (4) Date: Mar. 15, 2005

(87) PCT Pub. No.: WO03/051809

PCT Pub. Date: Jun. 26, 2003

(65) Prior Publication Data

US 2005/0171380 A1 Aug. 4, 2005

(30) Foreign Application Priority Data

Dec. 14, 2001 (EP) .................... 01129334

(51) Int. Cl.
*C07C 51/16* (2006.01)
(52) U.S. Cl. ...................... 562/545; 562/547
(58) Field of Classification Search ............ None
See application file for complete search history.

(56) References Cited

U.S. PATENT DOCUMENTS

| | | | |
|---|---|---|---|
| 4,147,885 A | 4/1979 | Shimizu et al. | |
| 4,306,088 A | 12/1981 | Nakamura et al. | |
| 4,365,087 A | 12/1982 | Kadowaki et al. | |
| 4,873,368 A | 10/1989 | Kadowaki et al. | |
| 5,077,434 A | 12/1991 | Sarumaru et al. | |
| 5,177,260 A | 1/1993 | Kawajiri et al. | |
| 5,218,146 A | 6/1993 | Takata et al. | |
| 5,426,221 A | 6/1995 | Willersinn et al. | |
| 5,785,821 A | 7/1998 | Sakamoto et al. | |
| 5,910,607 A | 6/1999 | Sakakura et al. | |
| 6,084,127 A | 7/2000 | Sakamoto et al. | |
| 6,498,272 B1 | 12/2002 | Schroeder et al. | |
| 6,646,161 B1 | 11/2003 | Eck et al. | |
| 6,679,939 B1 | 1/2004 | Thiel et al. | |

FOREIGN PATENT DOCUMENTS

| | | |
|---|---|---|
| DE | 3002829 | 7/1980 |
| DE | 3042468 | 6/1981 |
| DE | 4308087 | 9/1994 |
| DE | 19909923 A1 | 3/2000 |
| EP | 0274681 A1 | 7/1988 |
| EP | 0293224 A1 | 11/1988 |
| EP | 0427508 A1 | 5/1991 |
| EP | 0695736 B1 | 2/1996 |
| EP | 0778255 A1 | 6/1997 |
| EP | 0861820 | 9/1998 |
| GB | 1539671 A1 | 1/1979 |
| WO | WO 99/14182 | 3/1999 |

OTHER PUBLICATIONS

International Preliminary Examination Report mailed on Apr. 20, 2004 in PCT/EP02/14227.
International Search Report mailed on May 36, 2003 in PCT/EP02/14227.

*Primary Examiner*—Paul A. Zucker
(74) *Attorney, Agent, or Firm*—Smith Moore LLP

(57) ABSTRACT

The present invention relates to a process for the production of acrylic acid (AA) comprising the steps wherein: a) a 1st gas mixture comprising propylene, oxygen, an inert gas and steam is subjected to a 1st catalytic oxidation reaction stage thereby converting the propylene in the presence of a catalyst mainly into acrolein being contained in a 2nd gas mixture from said 1st catalytic oxidation reaction, b) said 2nd gas mixture from the 1st catalytic oxidation reaction stage is subjected to a 2nd catalytic oxidation reaction stage thereby converting the acrolein in the presence of a catalyst mainly into AA, being contained in a product gas, c) said product gas is subjected to a quench tower, wherein said AA is recovered as an aqueous solution comprising said AA being contained in the process water, wherein a process vent gas is obtained at the top of said quench tower, wherein, said 1st gas mixture has a steam/propylene ratio of >0.3 and <2 and, the amount of said process water is less or equal to the amount of water in said aqueous solution withdrawn from the quench tower.

22 Claims, 1 Drawing Sheet

PROCESS FOR THE PRODUCTION OF ACRYLIC ACID

Figure 1:
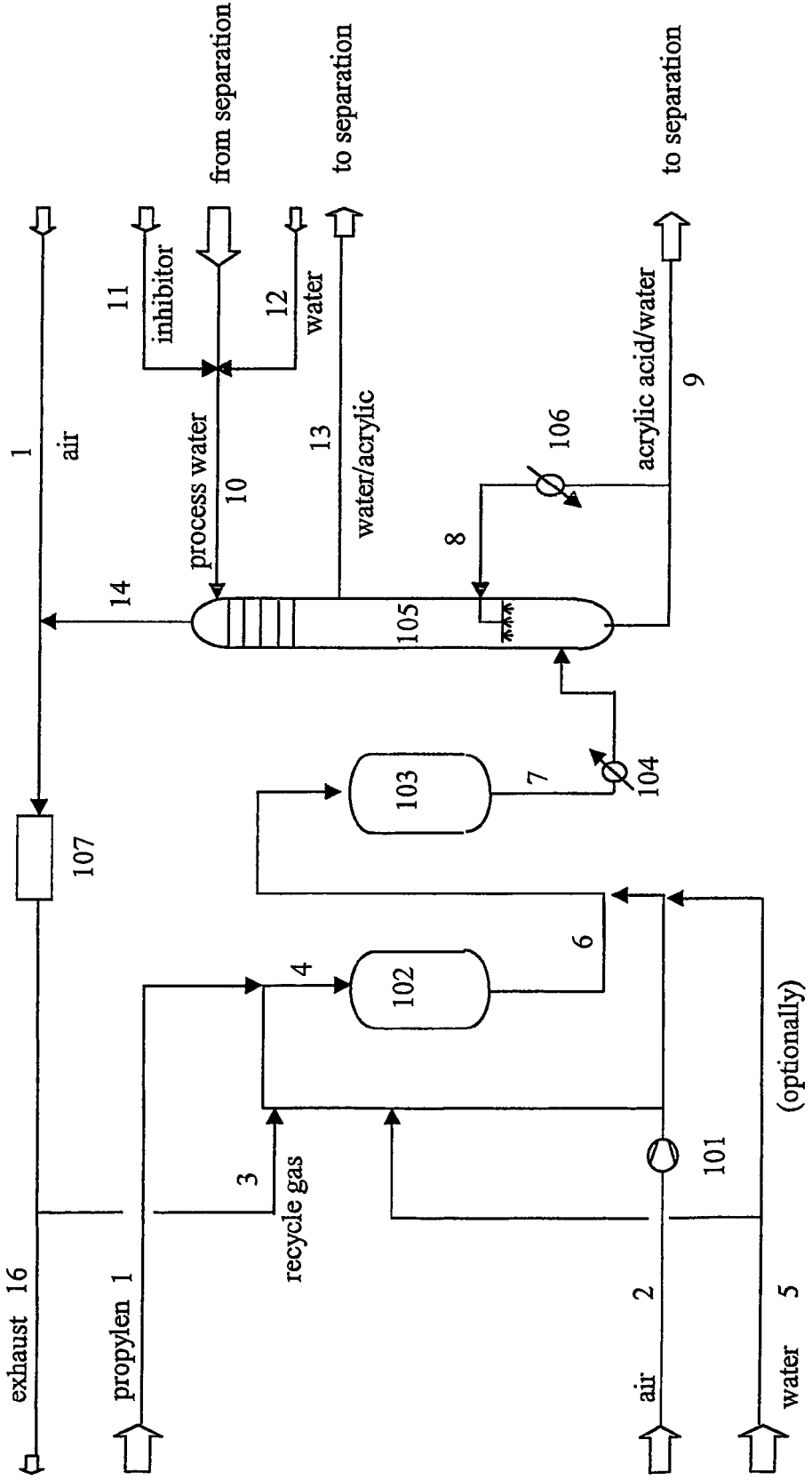

This application is a national stage application under 35 U.S.C. 371 of international application No. PCT/EP02/14227 filed Dec. 13, 2002, which is based on European application No. EP 011 29 334.7 filed on Dec. 14, 2001, and claims priority thereto.

The present invention relates to a process for the production of acrylic acid (AA) by catalytic vapor phase oxidation of propylene in two steps. The invention relates more particularly to a process for a very efficient production of a highly concentrated aqueous AA solution by oxidation of propylene at high concentration with high production rates and low emissions using recycled gas from a catalytic combustion unit by which nearly all organic compounds in the arising process vent gas and process water from propylene oxidation are removed.

The process for producing AA by the two-stage (the first catalytic oxidation reaction stage for conversion of propylene mainly to acrolein and the second catalytic oxidation reaction stage for conversion of acrolein to AA) catalytic vapor phase oxidation of propylene using molecular oxygen is already known and used on an industrial scale for several decades. For several reasons (flammable limits propylene/air, high heat of reaction) it is necessary to dilute the reaction gases by inert gases (e.g. water vapor, $N_2$, $CO_2$).

A typical process for industrial production is as follows. A mixture of propylene, air and steam is supplied to a first oxidation reactor and the propylene is converted mainly to acrolein and small amounts of AA in the first step. The product is supplied to a second oxidation reactor without separation. Fresh air and steam, if required for the subsequent oxidation reaction in the second oxidation step, can be added at the inlet of the second oxidation reactor.

For the separation of the gaseous AA from water vapor in the app. 180° C. effluent of the oxidation reactors two separation process routes are in use:
1. absorption of the gaseous AA in a high boiling hydrophobic aromatic solvent at temperatures that the process water will remain in the process vent gas leaving on the top of an absorption tower (see e.g. DE 43 08 087/BASF, 15 Sep. 1994)
2. absorption of the AA in water with simultaneous quenching to low temperatures in a quench tower/collector in such a way that nearly all of the vaporized process water in the 180° C. effluent of the second reactor will be condensed (see e.g. DE 30 42 468/Mitsubishi Chem. Corp. (MCC), 11 Nov. 1980).

Whereas in the first process route the AA and the high boiling products are separated in several distillation steps in the second process route after quenching, the water in the aqueous AA is separated in a subsequent azeotropic distillation to get crude AA, from which high purity AA for the production of AA copolymers or different AA esters are produced.

In the second process route, which will be regarded here, the handling of the process water, which consists of the water produced by the oxidation and the water necessary for dilution to be outside flammable limits has a remarkable influence on the economics of the process.

When the product gas containing AA obtained at the outlet of the second oxidation reactor is introduced into the quench tower to obtain AA as an aqueous solution, the resulting process vent gas containing unreacted propylene and other low boiling organic material is leaving at the top of the quench tower and has to be treated e.g. in an incinerator so that no or nearly no organic compounds are emitted into air (one pass through process).

It is also possible that a part of the process vent gas is recycled and added to the propylene/air/water stream at the inlet of the first reaction stage (cycle gas flow process) which is a quite common procedure especially in the case where the process is run with partial propylene conversion.

Improvements for this process have been proposed to produce AA more efficiently on a large scale by vapor-phase catalytic oxidation of propylene. Special improvements in this context are:

recycling the process vent gas to increase the concentration of AA in the bottom liquid of the quench tower by partly substituting the $H_2O$ vapor in the first stage reactor inlet stream by $N_2$ to operate outside flammable limits of propylene/air (see e.g. DE 30 02 829/MITSUBISHI PETROCHEMICAL Co. (MPCL), 26 Jan. 1980) and especially recycling the process water by separating the process water in a subsequent water separation unit (e.g. by azeotropic distillation). The process water is vaporized by using the heat of the hot effluent from the second oxidation reactor and is recycled as water vapor together with the process vent gas to the inlet of the first reaction stage. The not recycled part of this recycle stream is subjected to a thermal or catalytic combustion unit (see e.g. EP 0 695 736 B1/MITSUBISHI CHEMICAL Co., 4 Aug. 1995 or EP 0 778 255 A1/NIPPON SHOKUBAI Co., 5 Dec. 1996 or EP 0 861 820 A2/NIPPON SHOKUBAI Co., 27 Feb. 1998).

using under nearly complete propylene conversion a catalytic combustion unit to oxidize the organic compounds in the process vent gas from top of the quench tower upstream of the branch of the treated process vent gas (see e.g. EP 0 274 681 B1/MITSUBISHI PETROCHEMICAL Co., 10 Dec. 1987).

To use a catalytic combustion unit for the treatment of the organic compounds in the recycled process vent gas has several advantages. Besides that there is no special equipment (like a condenser) necessary to separate the acids in the recycle gas (mainly acrylic-, acetic- and propionic acid), which can damage the oxidation catalyst in the first catalytic oxidation reaction stage and reduce the life time of this catalyst, the $NO_x$ emissions of a catalytic combustion unit are more than 100 times less (<1 ppm) compared to a thermal combustion unit because of the much more lower temperature used during combustion (appr. 550° C.).

Up to today the process route with a catalytic combustion unit in the recycle gas is used only with recycled process vent gas and without recycling the process water. A further disadvantage is that the route is used only with low space time yield (STY) catalysts in the range of 0.16-0.17 kg AA/liter catalyst*h or low propylene space velocities ($SV_P$) in the range of 70 Nl propylene/l reaction volume $2^{nd}$ reaction stage. Together with a low organic combustion rate Pt catalyst in the catalytical combustion unit (see EP 0 274 681 B1/MITSUBISHI PETROCHEMICAL Co., 10 Dec. 1987), only low AA concentrations in the bottom liquid of the quench tower have been achieved.

Object of the present invention is to convert propylene to AA with high production rates together with long catalyst life time for the first and for the second catalytic oxidation reaction stage and together with high AA yield resulting in a high AA concentration in the quench tower bottom liquid in order to produce AA economically. Also treating the organic compounds in the process vent gas and process water with lowest possible $NO_x$ emissions is a necessary environmental issue today.

In the range of AA concentrations>80% by weight in the bottom liquid the absorption process of gaseous AA in the process water becomes ineffective and uneconomic because of the high number of trays needed (pinch effect). Accordingly it is a further object of the present invention to circumvent said pinch effect (see examples below).

From EP-A-0 274 681 a two step process for the production of AA is known. A gas mixture of propylene, molecular oxygen and an inert gas is subjected to 2 catalytic oxidation reaction stages. The resulting product gas is then subjected to an AA recovery step, in which the AA is recovered as an aqueous solution. The vent gas obtained from the AA recovery step is subsequently subjected to catalytic combustion and partially recycled to the $1^{st}$ catalytic oxidation reaction stage. However, this process has the disadvantage that the steam concentration in the gas mixture which is subjected to the $1^{st}$ catalytic oxidation must be as low as possible in order to increase the life of the Mo—Bi-based catalyst. Additionally the AA concentration in the aqueous solution is rather low by weight so that the subsequent separation of the water from the AA is very costly and a lot of waste water has to be treated. The space time yield (STY) obtained is 0.164 kg AA/liter catalyst*h.

GB-A-1539671 teaches a process for the production of AA from propylene via acrolein as an intermediate by catalytic vapor phase oxidation. The process comprises passing a starting reactant gas mixture through two catalytic oxidation reactors and introducing the resulting AA containing gas into an AA collector, thereby recovering the AA in the form of an aqueous solution. The exhausted gas from the collector is partially incorporated into the starting gas mixture. The process has the disadvantage that the recycled gas contains traces of unrecovered AA and acetic acid which deactivate the Mo—Bi based catalyst.

EP-A-0 778 255 discloses a process for producing AA by subjecting propylene and/or acrolein to catalytic gas phase oxidation. The AA containing gas thus obtained is contacted in a quench tower with an aqueous collecting agent comprising AA, acetic acid and a poorly water soluble solvent to recover the AA from the gas as an aqueous solution. This aqueous solution is then subjected to an azeotropic distillation in the presence of a poorly water soluble solvent to obtain high purity AA. This process has the disadvantage that only up to 90% of the aqueous solution resulting from the azeotropic distillation are recycled to the quench tower so that a part of the aqueous solution has to be treated as waste water.

WO 99/14182 relates to a method for the fractional condensation of a gas mixture which contains at least one other condensable consistent in addition to AA or methacrylic acid and which also has a high proportion of one or several non-condensable compounds. According to said method, the gas mixture is passed through a column with separation-efficient baffles and the condensable constituents are condensed out by cooling. However, this teaching suffers under a highly concentrated bottom liquid stream which contains AA of 40% by weight, is rejected and needs a high reflux ratio on column top and a high bottom temperature.

It is therefore the objective of the present invention to provide a superior industrial process for the production of AA which overcomes the disadvantages of the state of the art. This objective is achieved by the provision of a process for the production of AA comprising the steps wherein:

(a) a $1^{st}$ gas mixture comprising propylene, oxygen, an inert gas and steam is subjected to a $1^{st}$ catalytic oxidation reaction stage thereby converting the propylene in the presence of a catalyst mainly into acrolein being contained in a $2^{nd}$ gas mixture from said $1^{st}$ catalytic oxidation reaction, (b) said $2^{nd}$ gas mixture from the $1^{st}$ catalytic oxidation reaction stage is subjected to a $2^{nd}$ catalytic oxidation reaction stage thereby converting the acrolein in the presence of a catalyst mainly into AA, being contained in a product gas, (c) said product gas is subjected to a quench tower, wherein said AA is recovered as an aqueous solution comprising said AA being contained in the process water, wherein a process vent gas is obtained at the top of said quench tower, and optionally (d) said process water, separated in a subsequent separation unit (e.g. azeotropic distillation) is fed back into said quench tower so that most parts of the process water vaporized is mixed with the process vent gas leaving the quench tower on top and is treated together with the process vent gas in a subsequent thermal or catalytic combustion unit, characterized in that said $1^{st}$ gas mixture has a steam/propylene molar ratio of >0.3 and <2 and the amount of said process water is less or equal to the amount of water in said aqueous solution withdrawn from the quench tower.

The foregoing and other features, aspects, and advantages of the present invention will become better understood with regard to the following description, appended claims, and accompanying drawing where:

FIG. 1 is a schematic of the process to make acrylic acid of the present invention.

In a preferred embodiment of the present invention the process for the production of AA comprising the steps (a), (b), (c) and (d).

In a preferred embodiment of the present invention all process water that results from the separation of the AA contained in the aqueous solution is treated in a combustion unit, so that the entire AA production process is free from residual waste water which otherwise had to be treated in a subsequent unit (e. g. thermal or catalytic combustion unit, activated sludge). The process water is preferably added to the top of the quench tower for absorbing the AA out of the process gas of the $2^{nd}$ oxidation reaction stage.

Furthermore, it is preferred according to the invention that in a step (d) said process vent gas and the vaporized process water is subjected to a catalytic combustion unit yielding a combusted process vent gas and at least a part of said combusted process vent gas is recycled to said $1^{st}$ catalytic oxidation reaction stage.

The recycle gas ratio (rgr) is defined as molar ratio of stream 3 (recycle gas feed into inlet of first oxidation reaction stage) to the sum of propylene feed (stream 1), oxygen feed into inlet of first oxidation reaction stage and water feed into inlet of first oxidation reaction stage. The combusted process vent gas is recycled with a rgr of preferably 0.1-0.2, more preferably 0.13-0.25 and most preferably 0.15-0.40.

According to an embodiment of the present invention, the gas mixture which is subjected to the $1^{st}$ catalytic oxidation reaction stage comprises oxygen, propylene, an inert gas and steam. The inert gas and steam concentration at the $1^{st}$ stage reactor inlet is determined by the recycle gas stream. The concentration of the propylene in the gas mixture at the $1^{st}$ catalytic oxidation reaction stage inlet is preferably >9 Vol.-%, more preferably >11 Vol.-% and most preferably >14 Vol.-%. The molar ratio of oxygen/propylene is in the range of 1-3, preferably 1.2-2.5 more preferably 1.4-1.8 and most preferably 1.3-1.7. The molar ratio of steam/propylene is, according to the present invention, >0.3 and <2, preferably 0.5-1.5. The steam can be taken from a steam supply and is added to the gas mixture. Furthermore, it is preferred that said process water is at least a part, preferably at least 90% by weight, of the water separated from the aqueous solution comprising water and AA.

According to another embodiment of the present invention, the steam in the combusted gas is recycled to the $1^{st}$ catalytic oxidation reaction stage. The steam content in the combusted gas is adjusted by the temperature at the top of the quench tower and the amount of organic compounds in the process vent gas. The amount of water and the amount of inert gas in the gas mixture have to be adjusted such that the gas mixture is outside the exposable limits.

As inert gases $N_2$, $H_2O$ and $CO_2$ are preferred. More preferable, however, the combusted gas which comprises mainly $N_2$, $CO_2$ and steam is used as inert gas.

For the oxidation of the organics to $CO_2$ in the catalytic combustion unit it has been found, that catalysts based on titanium and oxygen comprising compounds as carriers, preferably catalysts based on $TiO_2$-carriers, are extraordinarily stable under these process conditions, superior to all other carriers with respect to long term thermal and chemical stability and resistance against thermal shock at high dispersion and, thus, high specific long term activity of the precious metal dispersion. Additionally it has been found, that catalyst carriers from anatase are especially advantageous because the catalysts prepared with these carriers show the highest long term stability, higher than with rutile or brookite based carriers.

Oxidation reactions on precious metals are very fast and thus undergo strong mass transport limitations if the precious metal is deposited all over the surface of the porous structure of the carrier. This occurs easily when the impregnation is simply done by soaking the carrier with a solution of a very stable precious metal compound. One further preferred feature of the oxidation catalyst is that the precious metal is applied in a thin shell. Commonly, if the catalyst carrier is not sufficiently reactive to precipitate the precious metal, e.g. by neutralization of an acidic solution, the carriers are impregnated with soluble alkaline compound in a primary step. Mostly, the precious metal compound is in this case of chloridic nature, e.g. hexachloroplatinic acid.

For oxidation reactions, however, the presence of chloride residues is detrimental because the oxidation is extremely inhibited. Therefore, the chlorides must carefully be washed out of the catalyst in this case. This way of "fast" precipitation of the precious metal is applicable for the impregnation of particulate catalysts. If monoliths in honeycomb form have to be impregnated, a lot of problems are obtained, e.g. by enrichment of the precious metal in the respective ends of the channels, leaving the middle of the channels nearly unimpregnated. This problem is less severe applying a dense, pore free monolith with a washcoat.

Because the reaction involves the handling of large volumes of off gas under recycling, very low pressure losses within the reactors are desired. This may, on the other side, preferably be achieved by the application of honeycomb shaped monolith carriers, which then are preferably equipped with precious metal in a thin shell, but also display a very even distribution of the metal on the surface of the channels. Preferably the honeycomb carrier has a low delta pressure of less than 20 mbar/m³, preferably less than 10 mbar/m³ and most preferably less than 3 mbar/m³.

These catalysts can preferably be obtained by impregnation of the carrier with a moderately unstable precious metal compound, establishing on one side an even distribution within the channels, on the other side a precipitation of the precious metal before the soluble compounds are diffused into the core of the walls. This is preferably done by impregnation with a metal nitrate solution of the metal used in the catalyst, received by dissolution of hexachloroplatinic acid in concentrated nitric acid. In a similar way also impregnation with mixtures of several precious metals may be done, e.g. by platinum and palladium, either subsequently or simultaneously. The advantage of such mixtures may be a lower inhibition of the catalyst by carbon monoxide, a phenomenon which is well known.

As catalysts for the $1^{st}$ stage catalytic oxidation reaction of propylene to acrolein usually Mo—Bi based catalysts are used. Mo—Co—Bi based catalysts are the more preferred catalysts. In the $2^{nd}$ stage catalytic oxidation reaction from acrolein to AA Mo—V based catalysts are usually used and Mo—V—Bi catalysts are more preferred catalysts. Furthermore, it is preferred that the catalysts are of the composite oxide type.

The catalytic oxidation reactions are preferably heterogeneously catalyzed reactions. The $1^{st}$ catalytic reactions takes place preferably at a high temperature salt bath temperature >250° C., more preferably in a range from 275 to 400° C. and most preferably in a range from 290 to 330° C. and the $2^{nd}$ catalytic reaction is preferably carried out at a high temperature salt bath temperature >180° C., more preferably in a range from 200 to 300° C. and most preferably in a range from 230 to 280° C.

In the process according to the present invention it is preferred that as a process feature the space velocity of propylene (SVp) in the $2^{nd}$ catalytic oxidation reactor is at least 160 h$^{-1}$. The propylene oxygen molar ratio in the $2^{nd}$ catalytic oxidation reactor is in the range of 0.1-0.9 at a propylene conversion of at least 90 mol-% at one propylene pass through with a selectivity of acrolein and AA with respect to propylene of at least 90 mol-% in the $1^{st}$ catalytic oxidation stage. The acrolein conversion in the $2^{nd}$ catalytic oxidation stage is at least 95 mol-% and the overall selectivity is at least 83 mol-%. It is further preferred that in the process according to the present invention all the above process features are fulfilled.

The product gas resulting from the $2^{nd}$ catalytic oxidation reaction stage is subjected to the bottom of a quench tower. In this quench tower, the AA is recovered from this product gas stream and withdrawn from the quench tower as an aqueous solution, which is then treated in a subsequent water/acrylic acid separation step. The process vent gas together with non-converted propylene and/or propane leaves the quench tower at the top and is then subjected to a catalytic combustion unit.

The AA produced together with process water and by-products is separated from the process water in a subsequent water separation column (e.g. by azeotropic distillation). This separated process water is recycled to the top of the quench tower where it is vaporized. After mixing with the vaporized process water, the vent gas is fed into the catalytic combustion unit, where organic compounds in the process vent gas are oxidized to $CO_2$. The concentration of the total organic residue (carbon dioxide, carbon monoxide, propylene, propane, acetic acid, acrylic acid, acrolein) in the process vent gas can range from 2 to 4 Mol-% and the concentration of acrylic acid in the total organic residue from 1 to 3 Mol-%.

According to the present invention, it is preferred that the quench tower is operated under steady state conditions, the aqueous solution withdrawn from the quench tower comprises >55% by weight, preferably >90% by weight AA.

In order to operate the quench tower with a rather small number of trays and to remove AA, acrolein, other impurities and water from the quench tower via the process vent gas, the temperature and the pressure at the top of the quench tower should be adjusted to 30-90° C., preferably 40-80° C. and 1-8 bar, preferably 1.05-6 bar, more preferably 1.1-1.5 bar, respectively.

The quench tower comprises a cooling and an absorption section, wherein the product gas is subjected to the cooling section in a product gas portion and a side stream leaves the quench tower in a portion above said product gas portion. The quench tower comprises two parts, an upper and a lower part. The upper part of the quench tower comprises preferably 20-40 theoretical plates. In a preferred embodiment of the present invention, these plates are realized with a packing like Sulzer BX, Montz-PAK type BSH or with Koch-Glitsch Gauze Packing BX. Montz-Thormann-plates can also be used. It is preferred that the lower part comprises an indirect cooling section and that the upper part comprises a direct cooling section. In the lower part of the quench tower the temperature of the gas from the $2^{nd}$ catalytic oxidation reaction stage is reduced, preferably to 70-90° C., by recycling a part of the sump in the lower part of the quench tower. Preferably this so called recycling stream has 10-60 times the amount of the aqueous solution stream being withdrawn from the sump of the quench tower for purification of the AA. The recycling stream is cooled in a heat exchanger to 60-80° C. The lower part of the quench tower is preferably equipped with spray nozzles and segment cascade trays, random packing or structured packing. However, the numbers of sections of the quench tower is not limited to two.

The side stream of water with AA is preferably taken out in the upper half, preferably upper third of the quench tower more preferably between tray No. 4 and No. 8 and most preferably No. 5 and No. 6 for circumvention of the pinch effect. This side stream is separated from at least a part of AA in a subsequent separation unit (preferable in an azeotropic distillation column) and then sent back to the top of the quench tower together with the process water main stream.

The process vent gas obtained from the quench tower is subjected to a catalytic combustion unit. The catalyst used in the catalytic combustion unit is preferably based on $TiO_2$ carriers. Even more preferably are pure anatase carriers. These carriers are very resistant against abrupt changes in the process conditions like temperature, pressure etc. The catalytic combustion reaction involves the handling of large volumes of off gas under recycling, so very low pressure losses within the catalytic combustion reactor is required (<10 mbar/m). This is achieved by the application of a honeycomb monolith carrier. This carrier is equipped with precious metal in a thin shell evenly distributed on the surface of the channels.

The impregnation of the carrier is carried out with a moderately unstable precious metal compound, establishing an even distribution of the precious metal within the channels of the carrier with a low penetration depth in the carrier. This is carried out e.g. by impregnation with a platinum nitrate solution, received by dissolution of hexachloroplatinic acid in concentrated nitric acid. A co-precipitation of a second noble metal e.g. Pd is carried out correspondingly.

The catalytic combustion reaction of the said process vent gas takes place preferably at 175 to 650° C., more preferably at 190 to 580° C. and most preferably at 230 to 550° C. The combustion rate of the said Pt-catalyst is preferably in the range from 100 to 500 and more preferably in the range from 100 to 250 g organic carbon/g Pt*h.

After the vent gas has been subjected to the catalytic combustion unit it is at least partially recycled to the gas mixture being oxidized in the $1^{st}$ catalytic oxidation reaction stage with a recycle ratio between 0.1 to 0.4 (recycle ratio=molar ratio of recycle gas stream/feed gas stream). In a preferred embodiment of the present invention, the amount of combusted, recycled vent gas is adjusted in such a way that no additional steam has to be added to the $1^{st}$ and $2^{nd}$ catalytic oxidation reaction stage.

The process according to the present invention has the advantage that the aqueous solution removed from the AA recovery step has a very high AA concentration so that the subsequent AA separation can be operated with a low energy consumption rate. Additionally, since all water from the AA separation is recycled to the AA recover step, no waste water is produced. In a preferred embodiment of the present invention no additional steam has to be added to the process, neither to the $1^{st}$ catalytic oxidation reaction stage nor to the $2^{nd}$ catalytic oxidation reaction stage.

A preferred embodiment of the process according to the present invention is shown in FIG. 1.

In the embodiment of the present invention shown in FIG. 1, propylene 1, air 2, compressed by air compressor 101 and an inert combusted process vent gas (recycle) 3, comprising mainly $N_2$, $CO_2$ and steam, are combined to a gas mixture 4 as inlet stream for the first stage oxidation reactor 102. If the steam concentration in the inert combusted process vent gas 3 is not high enough (e.g. during start up), additional steam 5 can be added from an outside steam source to the first stage inlet stream 4. The steam and the inert gas concentration in the gas mixture 4 have to be such that the gas mixture 4 is outside flammable limits.

The gas mixture 4 is fed into the $1^{st}$ catalytic oxidation reactor 102, where propylene is converted mainly to acrolein. The effluent gas from the $1^{st}$ catalytic oxidation reactor 102 is subjected to a $2^{nd}$ catalytic oxidation reactor 103 in which acrolein is converted mainly into AA. If needed, the oxygen concentration in the feed gas 6 can be increased by addition of air 2. Additional steam 5 can be added too, if necessary (e.g. during start up). The product gas stream 7 resulting from the $2^{nd}$ catalytic oxidation reactor 103 is cooled down in a heat exchanger 104 and then subjected to a quench tower 105.

From the sump of the quench tower an aqueous AA solution 9 comprising process water and the recovered AA is withdrawn and then subjected to a water separation (not shown). A part of the aqueous AA solution 8 is subjected to a cooling device 106 and fed to the lower section. In the water separation, the aqueous solution stream 9 is separated into an AA stream and a stream comprising process water and impurities with a low boiling point, which are sent back to the quench tower via line 10.

In the quench tower 105 the AA is absorbed by the recycled process water form the water separation. It is a feature according to a preferred embodiment of the invention that all process water leaving the quench tower via line 9 to the water separation unit is recycled to the quench tower via line 10. Optionally, a polymerization inhibitor 11 can be added to the process water.

From one of the trays in the upper section of the top of the quench tower an AA containing side stream 13 is sent to the subsequent water separation unit—e.g. the azeotropic water separation unit already cited—the AA removed from the product stream and the separated water sent back to the upper section of the quench tower via line 10.

The process vent gas 14 from the quench tower is subjected to a catalytic combustion unit 107 and a part of the combusted process vent gas 3 is recycled after cooling to the 1$^{st}$ catalytic oxidation reactor 102 as steam and inert gas supply. The rest of the combusted vent gas is discharged into the atmosphere via line 16. Additional air 15 can be added to the process vent gas 14 to adjust the combustion conditions.

The following Examples describe the present invention into more detail:

EXAMPLE 1

To a two stage oxidation reactor as described in FIG. 1 a gas mixture (feed gas) containing 0.990 kg/h of propylene ($SV_p$=166 h$^{-1}$, related to second reaction stage) and 4.890 kg/h of humidified air including 0.220 kg/h of water was introduced to the first stage reactor (propylene 10.1 Mol-%, oxygen (as air) 15.5 Mol-%, water 6.0 Mol-%). Additionally 1.650 kg/h of dry air was introduced to the second stage reactor. The oxidation reactors were charged with a commercially available Mo—Co—Bi based catalyst in the first stage and with a Mo—V—W based catalyst in the second stage.

Under the following conditions the yield of AA was 86.36 Mol-%, the conversion of propylene was 97.54 Mol-% and the conversion of acrolein was 97.57 Mol-%:

| | |
|---|---|
| High temperature salt bath temperature 1$^{st}$ stage: | 335.4° C. |
| High temperature salt bath temperature 2$^{nd}$ stage: | 296.3° C. |

The top of the quench tower was charged with 0.939 kg/h of process water including 0.005 kg/h of hydroquinone, resulting in a top temperature of 52.6° C. These conditions led to an AA concentration of 83.9% by weight in the bottom of the quench tower including 1.18% by weight of dimer AA.

The side stream taken out between tray 5 and 6 of the quench tower (1.164 kg/h) contains 5.89% by weight of AA and 0.83% by weight of acetic acid, from which after separation 0.939 kg/h of process water are sent back to the top of the quench tower.

To achieve complete catalytic combustion of the process vent gas 0.585 kg/h of dry air were added to the catalytic combustion unit. The combusted waste gas consists of 4.27 vol.-% of oxygen, 80.9 vol.-% of nitrogen, 3.72 vol.-% of carbon dioxide and 11.1 vol.-% of water. From this combusted waste gas stream 0.729 kg/h were fed as recycle gas into the first reaction stage. The molar ratio of recycle gas stream to feed gas stream was 0.16 leading to the following molar ratios of the feed gas composition at the first and second reactor inlet:

Feed gas composition at the first and second reactor inlet:

| | |
|---|---|
| oxygen (1$^{st}$ stage)/propylene: | 1.51 |
| oxygen (2$^{nd}$ stage)/propylene: | 0.51 |
| water (1$^{st}$ stage)/propylene: | 0.52 |
| recycle gas stream (1$^{st}$ stage)/feed gas stream: | 0.16 |

The space time yield obtained for AA was 0.230 kg/($1_R$h)[1]). The carbon balance is closed with a value of 0.7 Mol-%.

[1])R=total reaction volume of first and second stage reactors

EXAMPLE 2

To a two stage oxidation reactor as described in FIG. 1 a gas mixture (feed gas) containing 0.947 kg/h of propylene ($SV_p$=160 h$^{-1}$, related to second reaction stage) and 4.733 kg/h of humidified air including 0.687 kg/h of water was introduced to the first stage reactor (propylene 10.0 Mol-%, oxygen (as air) 15.3 Mol-%, water 17.0 Mol-%). Additionally 1.583 kg/h of dry air was introduced to the second stage reactor. The oxidation reactors were charged with a commercially available Mo—Co—Bi based catalyst in the first stage and with a commercially available Mo—V—W based catalyst in the second stage.

Under the following conditions the yield of AA was 88.44 Mol-%, the conversion of propylene was 98.73 Mol-% and the conversion of acrolein was 98.86 Mol-%:

| | |
|---|---|
| High temperature salt bath temperature 1$^{st}$ stage: | 353.6° C. |
| High temperature salt bath temperature 2$^{nd}$ stage: | 278.4° C. |

The top of the quench tower was charged with 0.537 kg/h of process water including 0.008 kg/h of hydroquinone, resulting in a top temperature of 51.7° C. These conditions led to an AA concentration of 68.8% by weight in the bottom of the quench tower including 0.57% by weight of dimer AA. Condensed phase of the process vent gas leaving the top of the quench tower (0.275 kg/h) contains 3.12% by weight of AA, the loss of AA yield via the top of the quench tower was 0.53 Mol-%.

The side stream taken out between tray 5 and 6 of the quench tower (0.879 kg/h) contains 14.4% by weight of AA and 0.71% by weight of acetic acid, from which after separation 0.450 kg/h are sent back to the top of the quench tower.

Feed gas composition at the first and second reactor inlet:

| | |
|---|---|
| oxygen (1$^{st}$ stage)/propylene: | 1.53 |
| oxygen (2$^{nd}$ stage)/propylene: | 0.51 |
| water (1$^{st}$ stage)/propylene: | 1.70 |
| recycle gas stream (1$^{st}$ stage)/feed gas stream: | 0 |

The space time yield obtained for AA was 0.226 kg/($1_R$h)[1]). The carbon balance is closed with a value of 2.86 Mol-%.

[1])R=total reaction volume of first and second stage reactors

EXAMPLE 3

To a two stage oxidation reactor as described in FIG. 1, a gas mixture (feed gas) containing 0.965 kg/h of propylene ($SV_p$=163 h$^{-1}$, related to second reaction stage) and 4.923 kg/h of humidified air including 0.173 kg/h of water was introduced to the first stage reactor. Additionally 1.304 kg/h of dry air was introduced to the second stage reactor. The oxidation reactors were charged with a commercially available Mo—Co—Bi based catalyst in the first stage and with a commercially available Mo—V—W based catalyst in the second stage.

Under the following conditions the yield of AA was 85.20 Mol-%, the conversion of propylene was 97.40 Mol-% and the conversion of acrolein was 98.95 Mol-%:

| | |
|---|---|
| High temperature salt bath temperature 1st stage: | 337.5° C. |
| High temperature salt bath temperature 2nd stage: | 289.0° C. |

The top of the quench tower was charged with 1.116 kg/h of process water including 0.045 kg/h of hydroquinone, resulting in a top temperature of 54.6° C. These conditions led to an AA concentration of 89.0% by weight in the bottom of the quench tower including 1.1% by weight of dimer AA. The condensed phase of the process vent gas leaving the top of the quench tower contains 3.00% by weight of AA, the loss of AA via the top of the quench tower was 1.19 Mol-%.

The side stream taken out between tray 5 and 6 of the quench tower (1.21 kg/h) contains 14.6% by weight of AA and 1.24% by weight of acetic acid.

To achieve complete catalytic combustion of the process vent gas 0.183 kg/h of dry air were added to the catalytic combustion unit. The combusted waste gas consists of 2.51 vol.-% of oxygen, 82.8 vol.-% of nitrogen, 4.40 vol.-% of carbon dioxide and 10.3 vol.-% of water. From this combusted waste gas stream 0.730 kg/h were fed as recycle gas into the first reaction stage. The molar ratio of recycle gas stream to feed gas stream was 0.13 leading to the following molar ratios of the feed gas composition at the first and second reactor inlet:

Feed gas composition at the first and second reactor inlet:

| | |
|---|---|
| oxygen (1st stage)/propylene: | 1.56 |
| oxygen (2nd stage)/propylene: | 0.41 |
| water (1st stage)/propylene: | 0.42 |
| recycle gas stream (1st stage)/feed gas stream: | 1.49 |

The space time yield obtained for AA was 0.221 kg/ $(l_R h)^1$. When comparing with the example 2, the inlet water concentration has been reduced from a molar ratio of 1.7 (water (1$^{st}$ stage)/propylene) to 0.42.

[1] $R$=total reaction volume of first and second stage reactors

The invention claimed is:

1. A process for the production of acrylic acid (AA) comprising the steps:
    (a) subjecting a first gas mixture comprising propylene, oxygen, an inert gas, and steam to a first catalytic oxidation reaction stage thereby converting the propylene in the presence of a catalyst mainly into acrolein being contained in a second gas mixture from said first catalytic oxidation reaction,
    (b) subjecting said a second gas mixture from the first catalytic oxidation reaction stage to a second catalytic oxidation reaction stage thereby converting the acrolein in the presence of a catalyst mainly into AA, being contained in a product gas,
    (c) subjecting said product gas to a quench tower, wherein said AA is recovered as an aqueous solution comprising AA being contained in the process water, wherein a process vent gas is obtained at the top of said quench tower, and wherein the process vent gas is treated in a subsequent thermal or catalytic combustion unit, and
    (d) separating said process water in a subsequent separation unit and process water is fed back into said quench tower so that most parts of the process water vaporized is mixed with the process vent gas leaving the quench tower on top and is treated together with the process vent gas in the thermal or catalytic combustion unit, wherein said first gas mixture has a steam/propylene ratio of greater than about 0.3 and less than about 2; and the amount of said process water is less or equal to the amount of water in said aqueous solution withdrawn from the quench tower; and wherein said treatment in said thermal or catalytic combustion unit yields a combusted process vent gas and at least a part of said combusted process vent gas is recycled to said first catalytic oxidation reaction stage.

2. The process of claim 1 wherein said catalyst of said first catalytic oxidation stage is a Mo—Co—Bi based catalyst.

3. The process of claim 1 wherein said catalyst of said second catalytic oxidation stage is a Mo—V—W based catalyst.

4. The process of claim 1 wherein a carrier for the catalysts in the catalytic combustion unit include $TiO_2$ carriers.

5. The process of claim 4 wherein said carrier is in the shape of honeycombs with a low delta pressure of less than about 20 mbar/m$^3$.

6. The process of claim 1 wherein the oxygen concentration in the second gas mixture can be increased by the addition of air.

7. The process of claim 6 wherein additional steam is added to the second gas mixture.

8. The process of claim 1 wherein the combusted vent gas is at least partially recycled to the gas mixture being oxidized in the first catalytic oxidation reaction stage.

9. The process of claim 1 wherein the concentration of the propylene in the gas mixture at the first catalytic oxidation reaction stage inlet is at least about 9 Vol.-%.

10. The process of claim 1 wherein said process water is at least a part, of the water from a separation of said AA comprising aqueous solution into water and AA.

11. The process of claim 1 wherein said quench tower comprises a cooling and an absorption section, wherein said product gas is subjected to said cooling section in a product gas portion and a side stream leaves the quench tower in a portion above said product gas portion.

12. The process of claim 1 wherein a side stream of water with AA is taken out in the upper half, wherein said side stream is separated from at least a part of AA in a subsequent separation unit then sent back to the top of the quench tower together with the process water main stream.

13. The process of claim 1 wherein the space velocity of propylene (SVp) in said second catalytic oxidation reactor is at least 160 h$^{-1}$ or the propylene oxygen ratio is in said second catalytic oxidation reactor is in the range of from about 0.1 to about 0.9 at a propylene conversion of at least about 90 Mol-% at one propylene pass through with a selectivity of acrolein and AA with respect to propylene of at least about 90 Mol-% in said first catalytic oxidation stage and the acrolein conversion in said second catalytic oxidation stage is at least about 95 Mol-% and an overall selectivity of at least about 83 Mol-%.

14. The process of claim 1 wherein the temperature at the top of the quench tower is in the range of from about 30 to about 90° C.

15. The process of claim 1 wherein the pressure at the top of the quench tower is from about 1 to about 8 bar.

16. The process of claim 4 wherein said carrier is in the shape of honeycombs with a low delta pressure of less than about 10 mbar/m$^3$.

17. The process of claim 4 wherein said carrier is in the shape of honeycombs with a low delta pressure of less than about 3 mbar/m$^3$.

18. The process of claim 1 wherein the concentration of the propylene in the gas mixture at the first catalytic oxidation reaction stage inlet is at least about 11 Vol.-%.

19. The process of claim 1 wherein the concentration of the propylene in the gas mixture at the first catalytic oxidation reaction stage inlet is at least about 14 Vol.-%.

20. The process of claim 1 wherein the temperature at the top of the quench tower is in the range of from about 40 to about 80° C.

21. The process of claim 1 wherein the pressure at the top of the quench tower is from about 1.05 to about 6 bar.

22. The process of claim 1 wherein the pressure at the top of the quench tower is from about 1.1 to about 1.5 bar.

* * * * *